(12) United States Patent
Wong

(10) Patent No.: US 7,214,939 B1
(45) Date of Patent: May 8, 2007

(54) ULTRA LOW POWER NDIR CARBON DIOXIDE SENSOR FIRE DETECTOR

(75) Inventor: Jacob Y. Wong, Goleta, CA (US)

(73) Assignee: Airware, Inc., Goleta, CA (US)

( * ) Notice: Subject to any disclaimer, the term of this patent is extended or adjusted under 35 U.S.C. 154(b) by 0 days.

(21) Appl. No.: 11/284,460

(22) Filed: Nov. 21, 2005

(51) Int. Cl.
*G01J 1/00* (2006.01)

(52) U.S. Cl. .......................... 250/339.15; 250/339.13; 250/339.01; 250/339.12; 250/339.03

(58) Field of Classification Search ........... 250/339.15, 250/339.3, 339.06, 339.03, 339.01, 339.12; 340/627, 328, 629
See application file for complete search history.

(56) References Cited

U.S. PATENT DOCUMENTS

| | | |
|---|---|---|
| 3,793,525 A | 2/1974 | Burch et al. |
| 3,811,776 A | 5/1974 | Blau et al. |
| 4,578,762 A | 3/1986 | Wong |
| 4,694,173 A | 9/1987 | Wong |
| 5,053,754 A | 10/1991 | Wong |
| 5,079,422 A | 1/1992 | Wong |
| 5,103,096 A | 4/1992 | Wong |
| 5,163,332 A | 11/1992 | Wong |
| 5,369,397 A | 11/1994 | Wong |
| 5,494,640 A * | 2/1996 | Simon et al. ............. 422/82.05 |
| 5,592,147 A | 1/1997 | Wong |
| 5,691,704 A | 11/1997 | Wong |
| 5,721,430 A * | 2/1998 | Wong ..................... 250/339.13 |
| 5,767,776 A | 6/1998 | Wong |
| 5,798,700 A | 8/1998 | Wong |
| 5,800,360 A * | 9/1998 | Kisner et al. ............... 600/532 |
| 5,945,924 A | 8/1999 | Marmon et al. |
| 5,966,077 A * | 10/1999 | Wong ......................... 340/630 |
| 6,107,925 A | 8/2000 | Wong |
| 6,166,647 A * | 12/2000 | Wong ......................... 340/628 |

FOREIGN PATENT DOCUMENTS

GB 2392721 A * 3/2004

* cited by examiner

*Primary Examiner*—David Porta
*Assistant Examiner*—Djura Malevic
(74) *Attorney, Agent, or Firm*—Wagner, Anderson & Bright, LLP; Roy L Anderson

(57) ABSTRACT

A fire detector and method for generating an alarm signal in response to a fire uses an NDIR $CO_2$ sensor to generate a detector signal based upon a 15µ absorption band of $CO_2$ and generates an alarm signal when a signal processor receives the detector signal and a preselected criterion is met that is indicative of the onset of a fire based upon an analysis of the detector signal using a detection algorithm that relies upon a trending pattern of the detector signal such as recognizing a substantial drop in the detector signal strength. The NDIR $CO_2$ sensor can also generate a reference detector signal based upon a 9.0µ neutral band with a FWHM=0.5µ while the signal processor utilizes a detection algorithm that is based upon a synchronized output signal representative of $CO_2$ concentration to generate an alarm signal when a preselected criterion indicative of the onset of a fire is met.

20 Claims, 5 Drawing Sheets

A schematic design and implementation of an ultra low power NDIR CO2 sensor deployed as a fire detector.

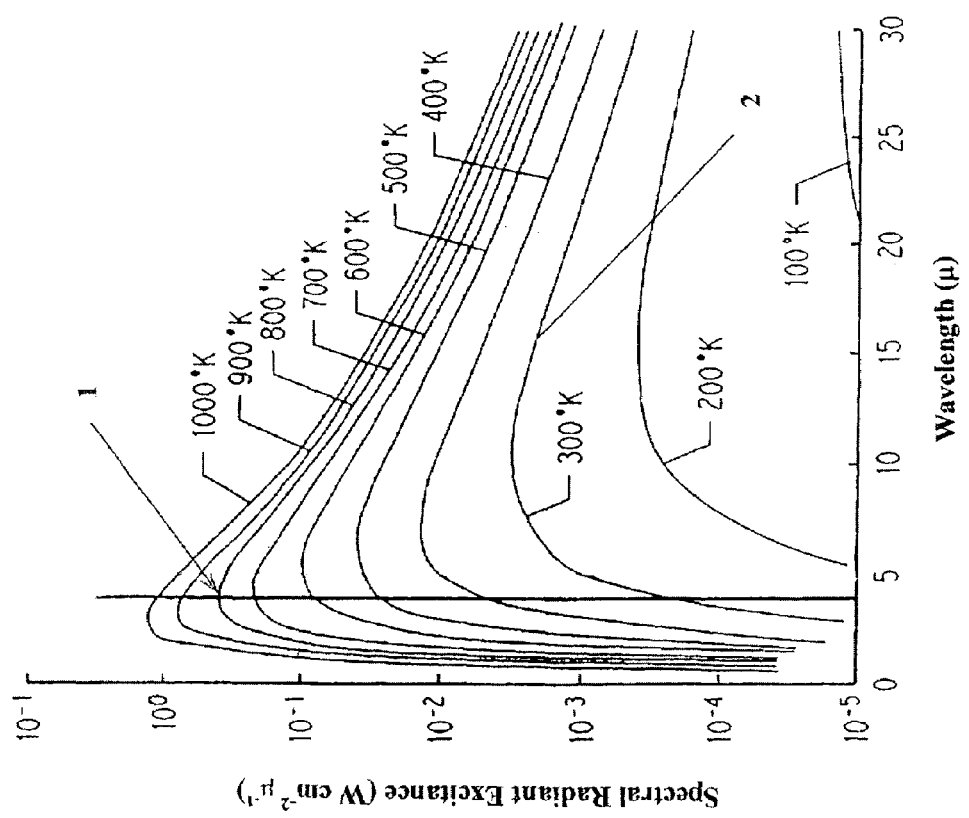
Figure 1. A graph showing the spectral radiant excitance of a blackbody source at temperatures 100 - 1,000 °K.

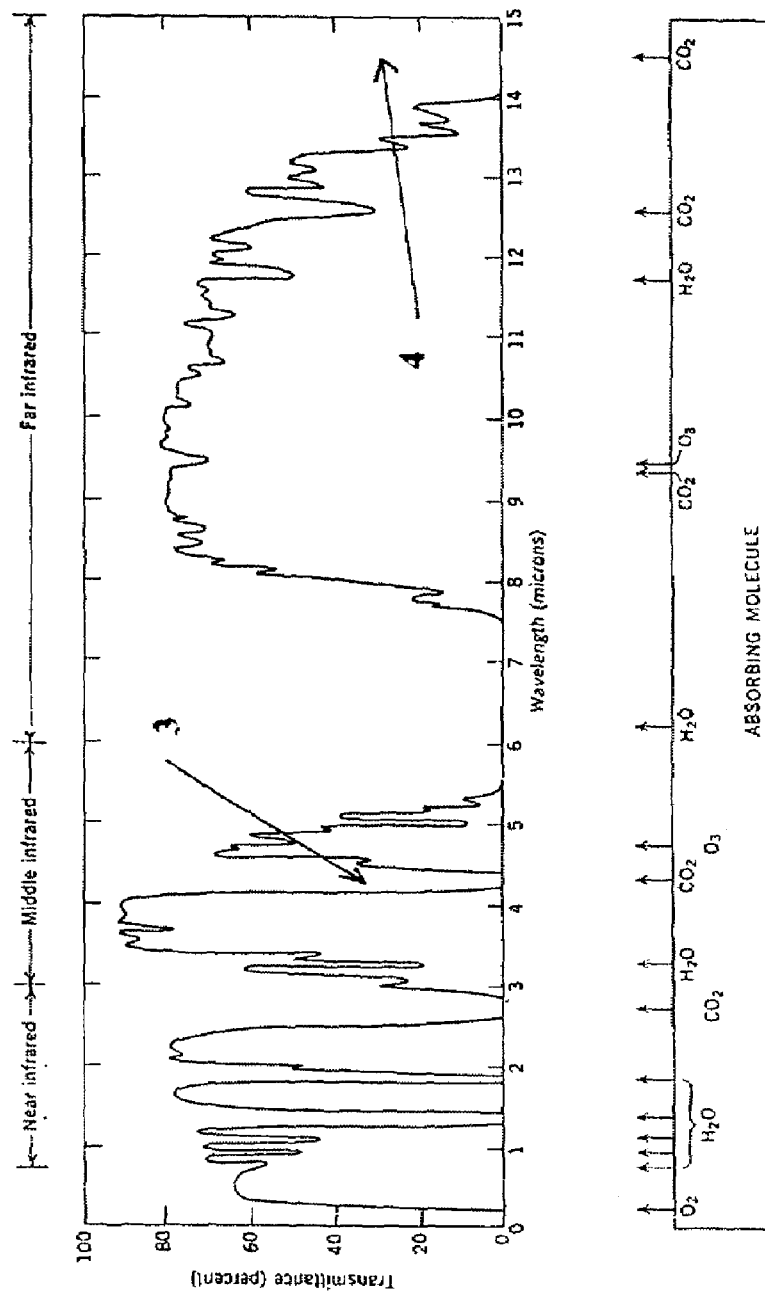
Figure 2. The transmittance of the atmosphere for a 6,000 ft. horizontal path at sea level showing the presence of the CO2 absorption bands at 4.26μ and ~15μ.

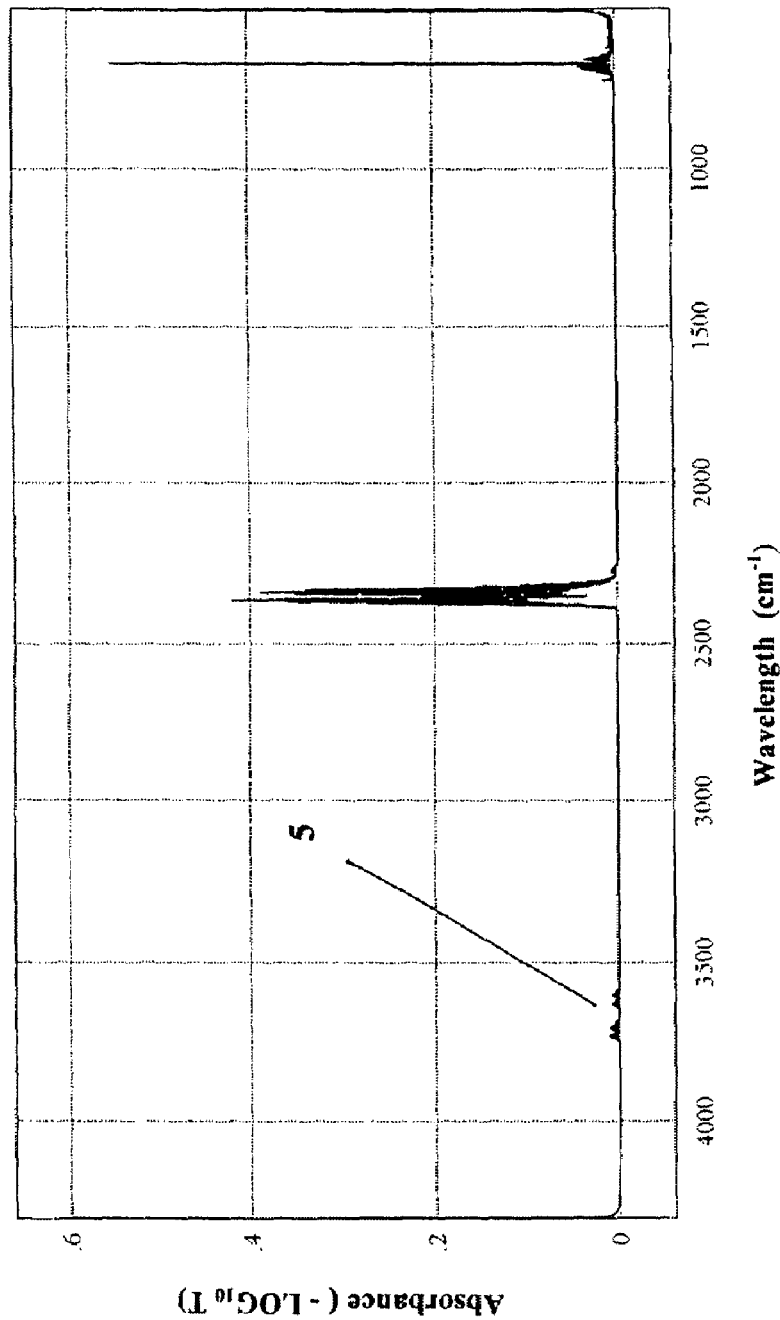
Figure 3. A schematic graph showing the absorbance of $CO_2$ gas at wavelengths from $2\mu - 20\mu$ ($5{,}000$ cm$^{-1}$ - $500$ cm$^{-1}$). Only the $4.26\mu$ and $\sim15\mu$ absorption bands of $CO_2$ are shown to be prominently present in this spectral region.

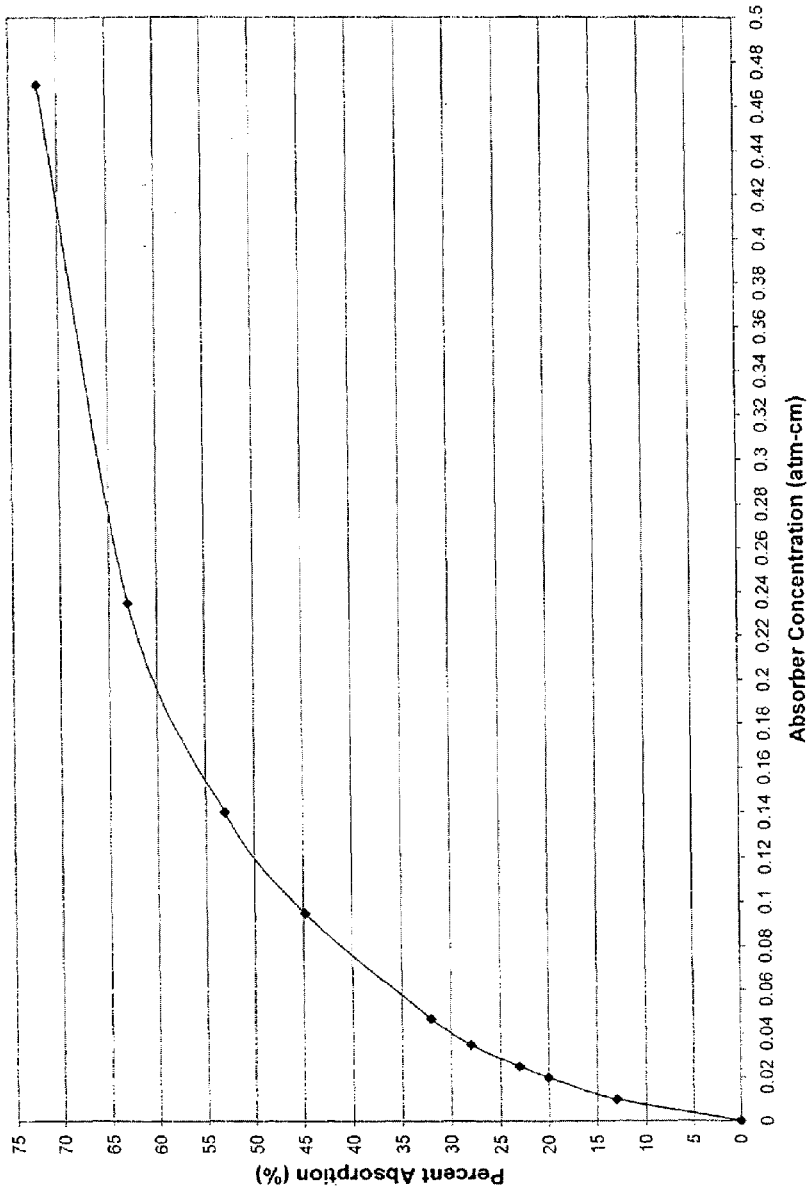
Figure 4. An experimentally measured percent absorption versus absorber concentration curve for the 4.26μ CO2 band with the use of a 0.14μ FWHM spectral filter. Similar results are expected of the ~15μ CO2 absorption band when an 1.0μ FWHM spectral filter is used.

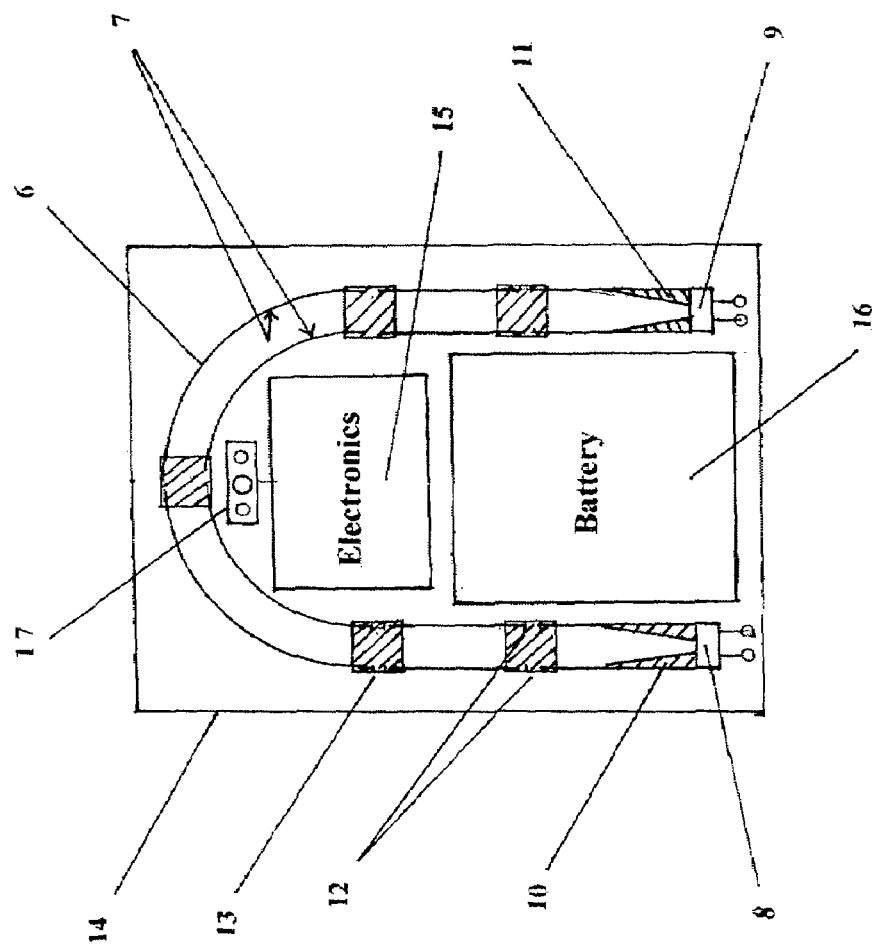
Figure 5. A schematic design and implementation of an ultra low power NDIR CO2 sensor deployed as a fire detector.

ULTRA LOW POWER NDIR CARBON DIOXIDE SENSOR FIRE DETECTOR

FIELD OF THE INVENTION

The present invention is in the field of gas analysis and more particularly relates to an ultra low power Carbon Dioxide ($CO_2$) sensor designed to be used as a compact, reliable, low cost, fast responding and false alarm resistant fire detector.

BACKGROUND OF THE INVENTION

The Non-Dispersive Infrared ("NDIR") technique has long been considered as one of the best methods for gas measurement. In addition to being highly specific, NDIR gas analyzers are also very sensitive, stable, reliable and easy to maintain. The major drawback of the NDIR gas measurement technique has been its relatively expensive implementation and high power consumption.

Ever since the NDIR technique of gas measurement was first introduced and practiced in the mid 1950's, a large number of improved measurement techniques based upon the NDIR principle for gas detection have been proposed and successfully demonstrated. The most notable advances over the years in this field are summarized as follows.

Burch et al. (U.S. Pat. No. 3,793,525) and Blau et al. (U.S. Pat. No. 3,811,776) in 1974 were the first to advance a so-called "Double Beam" technique for NDIR gas measurement by taking advantage of the principle of nonlinear absorption for some strongly absorbing gases such as $CO_2$ to create a reference channel. Shortly thereafter, this "Double Beam" NDIR gas sensor technique was greatly simplified with the use of two interposed spectral filters (one absorbing and one neutral) to create a sample and a reference detector channel. Subsequent NDIR gas sensors, designed using this technique, have enjoyed good output stability as a function of time.

In U.S. Pat. No. 4,578,762 (1986) Wong advanced the first self-calibrating NDIR $CO_2$ analyzer using a novel two-wheel chopper and mirror arrangement. Another improved type of such gas analyzer is shown and described in U.S. Pat. No. 4,694,173 (1987) by Wong. This gas analyzer has no moving parts for effecting the interposition of spectral filters or absorbing and non-absorbing cells to create both a sample and reference detector channel as in the NDIR gas analyzers described earlier.

In U.S. Pat. No. 5,163,332 (1992), Wong advanced the so-called "wave-guide" sample chamber for simplifying NDIR gas sensors into ones that are compact, rugged and low-cost while still maintaining their superior performance characteristics.

All of the NDIR gas analyzers described above for the measurement of the concentrations of one or more gases in a mixture perform well functionally and have contributed overwhelmingly to the overall technical advancement in the field of gas analysis during the past two decades. They have been widely accepted in both the medical and industrial communities. Despite their undisputed success over the years, there still remain a number of important applications, primarily in the industrial sector, where these NDIR techniques are still too complex, and hence too costly, to be taken advantage of. One such example is the methane gas detector for the miners. The ideal solution here is a small, very low cost and battery-operated methane gas sensor mountable directly below the headlight on the miner's helmet. In the event the miner encounters a methane gas pocket during excavation in the mine, this particular sensor can detect a dangerous level of the gas much sooner than the current setup in which a relatively bulky methane analyzer is normally located quite a distance behind the working miners. Furthermore, such a helmet-mounted methane gas sensor allows the alarm to be placed inside the helmet and close to the miner's ears thereby avoiding the tragic possibility that the alarm from a more remote methane analyzer might be drowned out by the machine noises in the mine.

Another example is the commonplace household fire detector. A majority of fire detectors in use today in almost all public buildings and private dwellings are in essence smoke detectors as they only detect the smoke resulting from a fire. The most common smoke detectors currently in use belong to two types. The first type is the so-called ionization smoke detector best for detecting invisible smoke particles ranging in size from <1.0 microns to ~5 microns. The second type is called the photoelectric smoke detector best for detecting visible smoke particles >5 microns in size. For the past two decades, the ionization smoke detectors because of their low cost (<$10 retail) have dominated the fire market and are in use in over 90% of households. In recent years, photoelectric smoke detectors, because of their higher cost (<$30 retail), have fallen significantly behind in sales. Combined ionization and photoelectric smoke detectors, albeit at an even higher cost (~$40 retail), have also been available for quite sometime but have not to date received much acceptance by the public.

Despite their low cost, relatively maintenance-free operation and wide acceptance by the buying public, the smoke detectors in widespread use today are not without problems and certainly are far from being ideal. One of the biggest problems with ionization smoke detectors besides being radioactive (Americium-241) is their frequent false-alarm. By the nature of its operational principle, any micron-size particulate matter other than smoke from an actual fire can set off the alarm. Kitchen grease particles generated by a hot stove is one classic example. Overzealous dusting of objects and/or furniture near the detector is another. Frequent false-alarms are not just a harmless nuisance; some people actually disable their smoke detectors by temporarily removing the battery in order to escape such annoying episodes. This latter situation could be outright dangerous especially when these people forget to rearm their smoke detectors.

Another significant drawback for the current ionization smoke detector is its relatively slow speed to alert people of a fire. There are several factors that contribute to this particular drawback. The first fact is the detector trigger threshold for smoke which directly affects its response time to the onset of a fire. No doubt a lower trigger threshold would mean a faster fire detector. However, it also means more frequent annoying false alarms for the user. The second factor is the particular placement of the detector with respect to the spot where fire breaks out. Unlike ordinary gases, smoke is actually a complex sooty molecular cluster that consists mostly of carbon. It is much heavier than air and thus diffuses much slower than the gases we encounter everyday. Therefore, if the detector happens to be at some distance from the location of the fire, it will be awhile before enough smoke gets into the sampling chamber of the smoke detector to trigger the alarm. A third factor is the nature or type of the fire itself. Although smoke usually accompanies fire, the amount produced can vary significantly depending upon the composition of the material that catches fire. For example, oxygenated fuels such as ethyl alcohol and acetone give less smoke than the hydrocarbon from which they are derived. Thus, under free-burning conditions oxygenated fuels such as wood and polymethylmethacrylate give substantially less smoke than hydrocarbon polymers such as polyethylene and polystyrene. As a matter of fact, a small number of pure fuels, namely carbon monoxide, formaldehyde, metaldehyde, formic acid and methyl alcohol, burn with non-luminous flames and do not produce smoke at all.

Since fire is an oxidation process, detection of a sudden increase in ambient $CO_2$ level, one of the three principal effluent gases of fire, is an effective way of detecting same. For the past 20 years, the use of $CO_2$ sensor as a standalone fire detector or in combination with smoke detectors has been continually advocated by experts as the most effective fire detector. The reason is two-fold. First, there is a significant advantage of using a $CO_2$ sensor rather than a smoke detector for fire initiation detection. The mobility of $CO_2$ as a gas is far greater than that for smoke which is much heavier. Therefore $CO_2$ diffuses from the fire to the detector in a much shorter time leading to a faster response time for enunciating fire. Second, over the past two decades, compact, low cost and reliable NDIR type $CO_2$ sensors have become readily available. As a matter of fact, over the same period of time, a large number of deployment schemes, fire fighting techniques and fire control strategies, which use either a standalone NDIR $CO_2$ sensor or in combination with smoke detectors, have been advanced. The most notable proposals of such are summarized as follows.

In U.S. Pat. No. 5,053,754 (1991), Wong advanced the first NDIR $CO_2$ sensor used as a standalone fire detector. A fire detection system using at least two NDIR $CO_2$ sensors positioned at spaced locations in an area for pin-pointing the exact origin of a fire was described in U.S. Pat. No. 5,079,422 (1992) by Wong. Meanwhile a standalone and compact low-cost fire detector which responds quickly to an increase in the concentration of $CO_2$ gas in the ambient air was advanced in U.S. Pat. No. 5,103,096 (1992) by Wong. In U.S. Pat. No. 5,369,397 (1994), an adaptive fire detector taking advantage of the capability of an NDIR $CO_2$ sensor for computing the rate of $CO_2$ increase to shorten the response time for enunciating the onset of a fire was also advanced by Wong. In U.S. Pat. No. 5,592,147 (1997), an NDIR $CO_2$ sensor used cooperatively in combination with a photoelectric smoke detector for significantly reducing false alarms was put forth by Wong. Also in 1997 and in U.S. Pat. No. 5,691,704, Wong disclosed another NDIR $CO_2$/photoelectric smoke detector combination fire detector with special software which can be designed into a single semiconductor chip for cost reduction and further false alarm improvement. In U.S. Pat. No. 5,767,776 (1998), Wong disclosed the design of an NDIR $CO_2$ and smoke detector combination which reduces the maximum average response time to less than 1.5 minutes. Further refinement of this design was described in U.S. Pat. No. 5,798,700 (1998) by Wong, U.S. Pat. No. 5,945,924 (1999) by Marman et al. and U.S. Pat. No. 5,966,077 (1999) by Wong. Finally, a method for dynamically adjusting criteria for detecting fire through smoke concentration using an NDIR $CO_2$ and smoke detector combination was described by Wong in U.S. Pat. No. 6,107,925 (2000).

Despite the continual and persistent advocacy of many fire experts that an NDIR $CO_2$ sensor, either as a standalone fire detector or in combination with a smoke detector, is better than present-day smoke detectors in both speed of response and proof against false alarms, it has yet to be exploited as a superior fire detector. The reasons are two-fold. First, even with the drastic cost reduction for present-day NDIR $CO_2$ sensors, the cost is still far too high when compared with ionization type smoke detectors. Second and by far the most significant is the fact that being an NDIR gas sensor, its active infrared source uses far too much power when operated continuously. Because of this, it is not suitable for use in almost any circumstance, whether it is residential, commercial or industrial.

Accordingly, there is a long felt need for an improved NDIR $CO_2$ sensor that can be used in a fire detector that is economical and can replace present day ionization fire detectors that have slower response times and suffer from environmental concerns due to their use of radioactive materials.

SUMMARY OF THE INVENTION

The present invention is generally directed to a fire detector that uses an NDIR $CO_2$ sensor that generates a detector signal based upon a 15μ absorption band of $CO_2$ and generates an alarm signal when a signal processor receives the detector signal and a preselected criterion is met.

In a first, separate group of aspects of the present invention, the signal processor relies upon a detection algorithm that is based upon a sudden drop of the detector output signal (e.g., when the drop is >20%) indicative of the onset of a fire.

In a second, separate group of aspects of the present invention, the NDIR $CO_2$ sensor further generates a reference detector signal based upon a 9.0μ neutral band, the signal processor utilizes synchronized signal processing from the detector signal and the signal processor relies upon a detection algorithm that is based upon a synchronized output signal representative of $CO_2$ concentration.

In a third, separate group of aspects of the present invention, the NDIR $CO_2$ sensor (which can be used as a standalone smoke detector or combined with a smoke detector) has a waveguide sample chamber (that can be U-shaped) with at least one opening covered with a thin filtering membrane (such as a few thousandths of an inch of polyethylene) that allows $CO_2$ molecules to diffuse freely into and out of the sample chamber but rejects dust, smoke and water particles from entering the sample chamber, a semiconductor blackbody source (with an infrared source temperature of approximately 350° K.) mounted in one end of the chamber and a detector (with a detector temperature of approximately 300° K.) equipped with a spectral filter mounted on the other end of the chamber.

In a fourth, separate group of aspects of the present invention, a fire detector uses a $CO_2$ sensor that generates a detector signal representative of attenuation of radiation observed normally from a source to the detector that has a $CO_2$ detector, a filter for a 15μ absorption band of $CO_2$ and electronics for receiving the detector signal and generating an alarm signal when a preselected criterion is detected by an algorithm based at least in part upon the detector signal. The $CO_2$ sensor can also have a second reference detector with a 9.0μ neutral band filter with a FWHM=0.5μ.

In a fifth, separate group of aspects of the present invention, a method for generating an alarm signal in response to a fire is based upon using a $CO_2$ sensor to generate a detector signal based upon a 15μ absorption band of $CO_2$ and generating the alarm signal when a preselected criterion indicative of the onset of a fire is met based upon an analysis of the detector signal. The analysis of the detector signal can be performed by using a detection algorithm that relies upon a trending pattern of the detector signal such as recognizing a substantial drop in the detector signal strength when $CO_2$ subsequently arrive near the sensor as the fire persists.

In a sixth, separate group of aspects of the present invention, a method for generating an alarm signal in response to a fire is based upon using a $CO_2$ sensor to generate both a detector signal based upon a 15μ absorption band of $CO_2$ and a reference detector signal based upon a 9.0μ neutral band with a FWHM of 0.5μ, generating a synchronized output signal representative of $CO_2$ concentration based upon the detector signal and the reference detector signal and then generating an alarm signal when a preselected criterion indicative of the onset of a fire is met based upon an analysis of the detector signal which is performed by using a detection algorithm that analyzes the synchronized output signal.

It is therefore the object of the present invention to advance a new design for an NDIR gas sensor aimed at further lowering its cost and, more importantly, reducing its power consumption so that it uses approximately the same power as an ionization smoke detector. It is a further object of the present invention to design such an NDIR gas sensor that is suitable for use as a low cost, false alarm resistant and fast response fire detector.

These and further objects and advantages will be apparent to those skilled in the art in connection with the drawings and the detailed description of the preferred embodiment set forth below.

BRIEF DESCRIPTION OF THE DRAWINGS

FIG. 1 is a graph showing the spectral radiant excitance of a blackbody source at temperatures 100–1,000° K.

FIG. 2 shows the transmittance of the atmosphere for a 6,000 ft horizontal path at sea level showing the presence of the $CO_2$ absorption bands at both 4.26μ and ~15μ.

FIG. 3 shows the absorbance of $CO_2$ gas at wavelengths from ~2μ–20μ (5,000 cm-1–500 cm-1). Only the 4.26μ and ~15μ absorption bands of $CO_2$ are shown to be prominently present in this spectral region.

FIG. 4 shows the experimentally measured percent absorption versus absorber concentration curve for the 4.26μ $CO_2$ band with the use of a 0.14μ FWHM spectral filter. Similar results are expected of the ~15μ $CO_2$ absorption band when a 1.0μ FWHM spectral filter is used.

FIG. 5 shows schematically the design and implementation of an ultra low powered NDIR $CO_2$ sensor deployed as a fire detector.

DETAILED DESCRIPTION OF THE INVENTION

Over the past three decades, the design of NDIR $CO_2$ gas sensors has invariably used the strong $CO_2$ absorption band at 4.26μ infrared. This band is not only strong, it is also very specific. In other words, no other gases, other than some extremely weak water vapor absorption continuum, have absorption bands within it. Thus, interferences caused by the presence of other gases to the $CO_2$ measurement are virtually nonexistent. In accordance with the conventional wisdom of NDIR sensor design, the most optimum infrared source to use for $CO_2$ detection should have a blackbody temperature at around 800–900° K., which has its peak spectral radiant excitance located at around 4.26μ according to Planck's Radiation Law. Because of the facts mentioned above, NDIR $CO_2$ sensors are not difficult to design and they were among the earliest NDIR gas sensors manufactured and available for sale to the public circa around mid 1950's. However, the use of a high temperature infrared source for the design of a NDIR $CO_2$ sensor using the 4.26μ absorption band is the main reason why the power consumption for such a sensor is invariably so high and cannot be easily lowered. Since most fire detectors have always been battery-operated, requiring very low power consumption for their continuous operation, this is also the principal reason why NDIR $CO_2$ sensors to date have not been used as fire detectors.

To overcome this seemingly untenable situation, I have turned in the present invention to finding another specific absorption band for $CO_2$ such that the operating temperature of an infrared source used for its detection can be much lower than that when the 4.26μ absorption band of $CO_2$ is used. Therefore, instead of using the strong 4.26μ absorption band of $CO_2$ to design the sensor of the present invention, I use the strong and much broader absorption band of $CO_2$ at 14.9–16.2μ which I shall refer to as the "absorption band at ~15.0μ" or "15μ absorption band of $CO_2$." This 15μ absorption band of $CO_2$ is also very specific. Furthermore, it actually is even slightly stronger than the 4.26μ one.

FIG. 1 shows the graph depicting the spectral radiant excitance of a blackbody source at temperatures 100–1,000° K. The peak spectral radiant excitance for a 800° K. blackbody is at 4.26μ which is also the center wavelength (CWL) for the 4.26μ absorption band of $CO_2$ as indicated by the vertical line 1. This confirms the fact that the optimum temperature of the an infrared source using the 4.26μ absorption band for designing an NDIR $CO_2$ sensor is ~800° K. Also shown in FIG. 1 is the Planck's radiation curve for a 300° K. blackbody 2, which has a peak spectral radiant excitance at ~10–15μ centering approximately on the 15μ absorption band of $CO_2$. This is the reason why a much lower temperature infrared source can be used just as efficiently for the design of an NDIR $CO_2$ sensor when the 15μ absorption band of $CO_2$ is used.

FIG. 2 shows the transmittance of the atmosphere for a 6,000 ft. horizontal path at sea level showing the presence of the $CO_2$ absorption bands at both 4.26μ, 3, and ~15μ, 4. A more quantitative portrayal for these two $CO_2$ bands is depicted in FIG. 3 where the absorbance of $CO_2$ is plotted against wavelength for a gas sample having an absorber concentration of 0.01 atm-cm in Nitrogen and at 1 atmosphere total pressure. One can see from FIG. 3 that these two $CO_2$ bands have roughly the same strength. One can also see from FIG. 3 that with the exception of a couple of weaker bands at ~2.70μ, 5, there are no other $CO_2$ absorption bands present in the spectral region of 2μ–20μ.

I will now compare quantitatively the tradeoff for the design of an NDIR $CO_2$ sensor between using the 4.26μ absorption band with an infrared source at 800° K. (Case 1) and the ~15μ absorption band with a 350° K. source (Case 2) in accordance with this invention. I shall use the amount of available power incident on the infrared detector as the tradeoff criterion since the same type of detectors will be used in both cases. For Case 1 using an 8 mm ID "waveguide" tube sample chamber design, we have the following sensor design parameters:

| | |
|---|---|
| Active infrared source temperature | 800° K |
| Effective source area | 4 mm$^2$ |
| Source emissivity | 0.95 |
| 4.26μ spectral filter FWHM | 0.14 μ |
| Spectral filter transmission efficiency | 0.8 |
| Distance between source and detector | 6 cm |
| Infrared detector | Thermopile |
| Detector temperature | 300° K |
| Detector sensitive area | 1.2 mm$^2$ |

Using the above specified design parameters, we have

| | |
|---|---|
| Spectral radiant excitance at 800° K and 4.26 µ | = 0.40 × 0.94 W cm-2 µ-1 = 0.376 W cm-2 µ-1 |
| Collection Efficiency | = 1.20/(π × 4 × 4) = 0.0239 |
| Incident power at infrared detector | = 0.376 × 0.04 × 0.95 × 0.14 × 0.8 × 0.0239 W = 3.80 × 10-5 W |

For Case 2 using a 4.76 mm ID U-tube sample chamber design with concentrator cones at both the source and the detector, the sensor design parameters are:

| | |
|---|---|
| Passive infrared source temperature | 350° K |
| Effective source area | 0.64 mm$^2$ |
| Source emissivity | 0.95 |
| 15.0µ spectral filter FWHM | 1.0 µ |
| Filter transmission efficiency | 0.8 |
| Distance between source and detector | 15 cm |
| Infrared detector | Thermopile |
| Detector temperature | 300° K |
| Detector sensitive area | 1.2 mm$^2$ |

Using the above specified design parameters, we have

| | |
|---|---|
| Spectral radiant excitance at 350° K and 15.0 µ | = 0.65 × 10-3 × 0.50 W cm-2 µ-1 = 3.25 × 10-4 W cm-2 µ-1 |
| Collection Efficiency | = 0.95 |
| Incident power at spectral detector | = 3.25 × 10$^{-4}$ × 0.64 × 10$^{-2}$ × 0.95 × 1.0 × 0.95 = 1.88 × 10-6 W |

Thus, I have shown that the incident power at the detector for Case 2 (350° K. infrared source with 15µ $CO_2$ absorption band) is ~20 times less than that for Case 1 (800° K. infrared source with 4.26µ absorption band). The issue at hand is not to compare the performance of Case 2 directly against Case 1, which is designed to be an excellent NDIR $CO_2$ sensor. Rather, whether the performance of Case 2 is adequate to detect $CO_2$ effluence from a fire as a fast and false-alarm resistant fire detector.

FIG. 4 shows an experimentally measured percent absorption versus absorber concentration curve for the 4.26µ $CO_2$ absorption band with the use of a 0.14µ FWHM (Full-Width at Half-Maximum) spectral filter. For the Case 1 design, a $CO_2$ sample of 2,000 ppm and a path length of 6 cm (see Case 1 sensor design parameters above), the absorber concentration is 2,000×10−6×6 atm-cm or 0.012 atm-cm, the expected percent absorption of the incident power is found from FIG. 4 to be ~15% or 0.15. Thus the available modulated signal power is 0.15×3.8×10-5 W or 5.70×10-6 W. But the noise power of the thermopile detector is typically 1.3×10-9 W/$\sqrt{Hz}$. Thus the expected S/N for a 10 Hz bandwidth system (noise 4.1×10$^{-9}$ W) is ~1,390. In other words, the sensor will be capable of detecting a minimum of 2,000/1,390 ppm or ~2 ppm, an excellent NDIR $CO_2$ sensor.

Although no experimental absorption data is presently available for the 15µ absorption band of $CO_2$, its band strength is slightly stronger than the 4.26µ band (see FIG. 3). Assuming that the strength of the 15µ band and the 4.26µ band is the same, a $CO_2$ sample of 2,000 ppm and a path length of 15 cm (see Case 2 sensor design parameter above), the absorber concentration is 2,000×10$^{-6}$×15 atm-cm or 0.03 atm-cm, the expected percent absorption of the incident power is found from FIG. 4 to be ~25% or 0.25. Thus the available modulated signal power is 0.25×1.88×10$^{-6}$ W or 4.7×10$^{-7}$ W. Since the noise power is the same as in Case 1 or 4.1×10$^{-9}$ W, the expected S/N is 115. In other words, the Case 2 sensor will be able to detect a minimum of 2,000/115 ppm or 17 ppm which is more than adequate to detect the sudden rise of effluent $CO_2$ concentration (typically in hundreds or thousands of ppm's depending upon the type of fire) for enunciating a fire.

I have shown in the above paragraphs that by using the 15µ absorption band of $CO_2$ and a low temperature (350° K.) infrared source in accordance with the present invention it is possible to drastically reduce the power consumption for an NDIR $CO_2$ sensor so that it can be used a fire detector. However such is not the case when a low temperature (350° K.) infrared source is used with the 4.26µ absorption band. The available spectral radiant excitance at 4.26µ is more than 1,200 times less at 350° K. than at 800° K. Thus the previously insurmountable barrier which has long prevented NDIR $CO_2$ sensors from being used as fire detectors because of its high power consumption has now been removed.

Let me now compute the amount of power required to operate the above designed (Case 2) NDIR $CO_2$ sensor used as a fire detector. Since the power consumption by the infrared source far outweighs the electronic circuits required to operate the sensor as a fire detector (typically a few µA at 5V), one needs only to calculate the power consumption of the infrared source as follows.

| | |
|---|---|
| Volume of silicon infrared source | = 0.8 mm × 0.8 mm × 0.3 mm = 0.192 mm$^3$ = 1.92 × 10$^{-4}$ c.c. |
| Density of silicon | = 2.35 gm/c.c. |
| Mass of infrared source | = 1.92 × 10$^{-4}$ × 2.35 gm = 4.51 × 10$^{-4}$ gm |
| Specific heat of silicon | = 0.210 cal/gm or 0.878 J/gm |
| Heat required to raise mass by 50° C. | = 0.878 × 4.51 × 10$^{-4}$ × 50 J = 1.98 × 10$^{-2}$ J |
| Power raised in one second | = 1.98 × 10$^{-2}$ W |
| Pulsing the source once every 20 sec. at a duty factor of 20%, the power required | = 1.98 × 10$^{-2}$ × (1/20) × 0.2 W = 1.98 × 10$^{-4}$ W |
| Current drawn at a 9V battery | = 22 × 10$^{-6}$ A or 22 µA |
| Operating life of 9V battery (0.5 A-Hr) | = ~2.59 years |

Let me now describe in more detail an NDIR $CO_2$ sensor I have specially designed to be used as a fire detector in accordance with the present invention. FIG. 5 shows schematically the implementation of such a sensor. The sample chamber 6 is of a modified single U-bend tube design having an overall length of ~15 cm. It is extruded from aluminum with a typical OD of 0.313" (7.9 mm) and an ID of 0.187" (4.7 mm). The extrusion process renders the inner surface 7 of the sample chamber 6 specularly reflective with a reflectivity for infrared wavelengths >10µ greater than 0.95. A semiconductor blackbody source packaged in a TO-18 can 8 is mounted at one end of the U-tube sample chamber 6. A thermopile detector equipped with a spectral filter (CWL=15.1µ and FWHM=1.0µ) hermetically sealed as a window is packaged also in a TO-18 can 9 and is located at the other end of the U-tube sample chamber 6. Special conical concentrators 10 and 11 are respectively installed near the source 8 and detector 9 in order to enhance the throughput of radiation from the source 8 to the detector 9.

A number of hole-pairs (hole diameter typically 0.063" or 1.6 mm) 12 are fabricated approximately equidistant to one another along the U-tube sample chamber 6 as depicted in FIG. 5. Each of these hole-pairs is covered with a thin filtering membrane 13 (such as polyethylene) a few thousandths of an inch thick. This filtering membrane 13 is designed to allow only $CO_2$ molecules to diffuse freely into and out of the U-tube sample chamber 6 but reject dust particles of all sizes (including smoke particles from a fire) and other molecules such as $H_2O$ from entering same. Thus the reflective surface 7 and windows of active components, such as the source 8 and detector 9, of the U-tube sample chamber 6 are protected against possible obscuration via contamination from the ambience. The U-tube sample chamber 6 is mounted directly onto a printed circuit board (PCB) 14 which also houses the signal processing electronic circuits 15 and a battery 16. In normal operation, the sensor is powered by the battery 16. Additional input/output pins 17 are available for bringing in external power source to operate the sensor and also for alarm enunciation networking if necessary.

As alluded to earlier, numerous methodologies and application strategies for using conventional or standard NDIR $CO_2$ sensors as fire detectors, either singly or in combination with a smoke detector, have been advanced during the past 20 years. Accordingly, there will be no problem at all in using the presently invented ultra low power $CO_2$ sensor as a fire detector according to these teachings. However, in order to fully exploit the current invention, that is, to simplify its design and implementation as much as possible in order to minimize its production cost in addition to reducing its power consumption, a specific fire detection algorithm will be beneficial.

The currently invented ultra low power NDIR $CO_2$ sensor can just be a single-beam sensor without a reference wavelength channel such as at 9.0µ (see FIG. 2). The reason is that the fire threshold for the current $CO_2$ sensor when used as a fire detector is the detection of a sudden rise in $CO_2$ concentration in its vicinity. As long as such a sudden increase in $CO_2$ level is detected and enunciated as the initiation of a fire, the knowledge of the exact $CO_2$ concentration then prevailing is not necessary. Thus there is no need to calibrate the current $CO_2$ sensor. Furthermore, a viable algorithm to be used in the enunciation of a fire for the current fire detector can be based upon the detection of a sudden violent drop in the then-prevailing detector signal, such as in excess of 20%. The detector signal drop due to the presence of $CO_2$ gas in the vicinity of the sensor will be very significant in view of the strong 15µ $CO_2$ absorption band. This detector output drop would represent a sudden buildup of $CO_2$ in the vicinity of the sensor indicative of the onset of a fire. The normal time variant detector output signal is of no significance to the current fire detection algorithm as long as its magnitude or level stays within a proper voltage range by design. Thus there is no need to use a second reference channel in order to stabilize its output over time.

It is clear that when an NDIR $CO_2$ sensor does not require a reference channel (i.e. a single-beam instead of double-beam implementation) for it operation and also does not need to be calibrated to function as a fire detector, the sensor circuit will be very much simplified and its production cost will also be greatly reduced. Thus the presently invented ultra low power NDIR $CO_2$ sensor affords the lowest possible power consumption in addition to the lowest possible cost. Although the $CO_2$ sensor of the present invention can be employed by itself as a standalone fire detector, it can also be combined, if desired, with other smoke detectors as already taught in the art, While the invention has been described herein with reference to certain examples, those examples have been presented for illustration and explanation only, and not to limit the scope of the invention. Additional modifications and examples thereof will be obvious to those skilled in the art having the benefit of this detailed description. Further modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions as defined by the following claims.

What is claimed is:

1. A fire detector, comprising:
   an active source;
   an NDIR $CO_2$ sensor that generates a detector signal based upon a 15µ absorption band of $CO_2$; and
   a signal processor which receives the detector signal and generates an alarm signal when a preselected criterion is met.

2. The fire detector of claim 1, wherein the signal processor relies upon a detection algorithm that is based upon a sudden drop of the detector output signal indicative of the onset of a fire.

3. The fire detector of claim 2, wherein the detector signal drop is excess of 20% from the then prevailing signal level.

4. The fire detector of claim 1, wherein the NDIR $CO_2$ sensor is comprised of:
   a waveguide sample chamber with at least one opening covered with a thin filtering membrane that allows $CO_2$ molecules to diffuse freely into and out of the sample chamber but rejects dust, smoke and water particles from entering the sample chamber;
   a semiconductor blackbody source mounted in one end of the chamber; and
   a detector equipped with a spectral filter mounted on the other end of the chamber.

5. The fire detector of claim 4, wherein the thin filtering membrane is made of polyethylene and is approximately a few thousandths of an inch thick.

6. The fire detector of claim 5, wherein the waveguide sample chamber has a U-shape.

7. The fire detector of claim 4, wherein the blackbody source has an infrared source temperature of approximately 350° K.

8. The fire detector of claim 7, wherein the detector temperature is approximately 300° K.

9. The fire detector of claim 1, wherein the NDIR $CO_2$ sensor further generates a reference detector signal based upon a 9.0µ neutral band with a FWHM=0.5µ.

10. The fire detector of claim 9, wherein the signal processor utilizes synchronized signal processing from the detector signal.

11. The fire detector of claim 10, wherein the signal processor relies upon a detection algorithm that is based upon a synchronized output signal representative of $CO_2$ concentration.

12. The fire detector of claim 1, wherein the NDIR $CO_2$ sensor is used as a standalone smoke detector.

13. The fire detector of claim 1, wherein the NDIR $CO_2$ sensor is combined with a smoke detector.

14. A method for generating an alarm signal in response to a fire, comprising the steps of:
   using a $CO_2$ sensor and an active source to generate a detector signal based upon a 15µ absorption band of $CO_2$; and generating the alarm signal when a preselected criterion indicative of the onset of a fire is met based upon an analysis of the detector signal.

15. The method of claim 14, wherein the analysis of the detector signal is performed by using a detection algorithm that relies upon a trending pattern of the detector signal.

16. The method of claim 15, wherein the trending pattern includes a substantial drop in the detector signal strength when $CO_2$ subsequently arrive near the sensor as the fire persists.

17. The method of claim 14, comprising the further steps of:

using the $CO_2$ sensor to generate a reference detector signal based upon a 9.0μ neutral band with a FWHM=0.5μ; and generating a synchronized output signal representative of $CO_2$ concentration based upon the detector signal and the reference detector signal.

18. The method of claim 17, wherein the analysis of the detector signal is performed by using a detection algorithm that analyzes the synchronized output signal.

19. A fire detector, comprising:

a $CO_2$ sensor that generates a detector signal representative of attenuation of radiation observed normally from an active source to the detector based upon a 15μ absorption band of $CO_2$, comprising:

a $CO_2$ detector;

a battery source for powering the fire detector;

a filter for the 15μ absorption band of $CO_2$; and electronics for receiving the detector signal and generating an alarm signal when a preselected criterion is detected by an algorithm based at least in part upon the detector signal.

20. The fire detector of claim 19, wherein the $CO_2$ sensor is further comprised of:

a second reference detector; and a 9.0μ neutral band filter with a FWHM of =0.5μ.

* * * * *